United States Patent [19]

Liston

[11] 4,051,047

[45] Sept. 27, 1977

[54] GROUP II METAL MIXED SALTS OF TWO DIFFERENT ORGANIC ACIDS IN LUBRICANT

[75] Inventor: Thomas V. Liston, San Rafael, Calif.

[73] Assignee: Chevron Research Company, San Francisco, Calif.

[21] Appl. No.: 670,515

[22] Filed: Mar. 24, 1976

[51] Int. Cl.$^2$ .................... C10M 1/40; C10M 3/34; C10M 5/22; C10M 7/38
[52] U.S. Cl. .................... 252/33; 252/389 R
[58] Field of Search .................... 252/33, 389 R

[56] References Cited

U.S. PATENT DOCUMENTS

| | | | |
|---|---|---|---|
| 3,081,176 | 3/1963 | Rue | 252/33 |
| 3,197,406 | 7/1965 | Konecky et al. | 252/33 |
| 3,291,750 | 12/1966 | Maurer et al. | 252/33 |
| 3,431,265 | 3/1969 | Wakeman | 252/33 |
| 3,954,639 | 5/1976 | Liston | 252/33 |

Primary Examiner—Delbert E. Gantz
Assistant Examiner—Irving Vaughn
Attorney, Agent, or Firm—C. J. Tonkin; J. J. DeYoung

[57] ABSTRACT

Group II metal mixed salts of: (A) an oil-soluble hydrocarbyl sulfonic acid; and (B) a polyoxyalkylenated sulfuric acid are useful as rust inhibitors in lubricating oil compositions.

17 Claims, No Drawings

GROUP II METAL MIXED SALTS OF TWO DIFFERENT ORGANIC ACIDS IN LUBRICANT

BACKGROUND OF THE INVENTION

Field of the Invention

This application relates to new Group II metal salts for use in lubricating oil compositions. More specifically, it relates to the use of certain Group II metal salts as rust inhibitors in lubricating oil compositions.

Automotive lubricating oils are employed both for lubrication and as a vehicle for additives which serve to protect the lubricated surfaces against such deleterious processes as rust and corrosion, and the deposition of varnish. An important means for inhibiting rust and corrosion involves the rapid neutralization of acidic products of oil and fuel oxidation by lubricating oil additives or combinations of additives.

SUMMARY OF THE INVENTION

The Group II metal salts of this invention are salts of: (A) an oil-soluble hydrocarbyl sulfonic acid; and (B) a polyoxyalkylenated sulfuric acid having a molecular weight in the range from about 500 to about 5000.

These Group II metal salts are useful in the preparation of improved lubricating oil compositions. They provide rapid neutralization of aqueous acid and rust protection for internal combustion engines.

In its broadest aspect, the lubricating oil composition of this invention comprises an oil of lubricating viscosity and a rust-inhibiting amount of said Group II metal salt.

DESCRIPTION OF PREFERRED EMBODIMENTS

The Group II metal salts of this invention are mixed salts of an oil-soluble hydrocarbyl sulfonic acid and a polyoxyalkylenated sulfuric acid having a molecular weight in the range from about 500 to 5000.

The oil-soluble hydrocarbyl sulfonic acid includes any sulfonic acid whose salt is useful as a detergent or dispersant in lubricating oil compositions. Preferably the sulfonic acid is a petroleum sulfonic acid, a polyalkylbenzene sulfonic acid or a polyalkylene sulfonic acid.

The oil-soluble hydrocarbyl sulfonic acids include those which can be formed from the sulfonates derived from mahogany acids, i.e., the mahogany-colored petroleum sulfonic acids obtained as a by-product during white oil manufacture. A general review of the preparation of petroleum sulfonates and their use as lubricating oil additives can be found in National Petroleum News, 37, No. 40, pages R793-R800, Oct. 3, 1945, the disclosure of which is hereby incorporated by reference.

The polyalkylbenzene sulfonates are derived from longchain alkyl-substituted benzenes, principally the polydodecylbenzene bottoms obtained as by-products in the manufacture of household detergents. The preparation of polyalkylbenzene sulfonates and their use in lubricating oils is described in Belgian Pat. No. 629,945, U.S. Pat. No. 2,924,617, U.S. Pat. No. 2,982,726 and British Pat. No. 844,335. The disclosures of these patents are incorporated herein by reference.

The polyalkylene sulfonates are polyolefin-derived sulfonates which can be prepared, for example, by treating a polyolefin with chlorosulfonic acid, sulfur trioxide and hydrogen chloride, sulfuric acid, sulfuric acid with $SO_3$, $SO_3$, $SO_2$ and oxygen, etc. A typical preparation of polyisobutenyl sulfonate is shown in British Pat. No. 1,246,545, in which polyisobutylene with average molecular weight of 950 is first chlorinated and then treated with chlorosulfonic acid, lime and ethylene glycol to yield a calcium polyisobutenyl sulfonate.

The polyoxyalkylenated sulfuric acid (or salt thereof) used in the preparation of the salts of this invention have a total molecular weight after sulfation of about 500 to about 5000. The preferred embodiments are described as the alcohols and aromatic hydroxy compounds from which they are derived, as the oxyalkylenated alcohol or oxyalkylenated aromatic hydroxy compound from which they are derived, or as the sulfuric acid which per se or as its salts is one of the reactants used to form the mixed salt of this invention.

The oxyalkylenated alcohols and aromatic hydroxy compounds which may be sulfated to produce the auxiliary rust inhibitors of the present invention are derived from hydroxy compounds which are substantially aliphatic compounds such as monohydric and polyhydric alcohols or substantially aromatic (hydroxy) compounds such as the substituted phenols. The aromatic hydroxy compounds from which the oxyalkylenated sulfates of the invention may be derived are illustrated by such compounds as phenol, cyclohexylphenol, di(hydroxyphenyl) disulfide, di(hydroxyphenyl) sulfide, di(hydroxyphenyl) oxide, the condensation product of octylphenol with acetone, benzyl alcohol, the condensation product of heptylphenol with formaldehyde, polyisobutene-substituted phenol having a molecular weight of about 1000, xylylene glycol, 4,4'-methylene-bis-phenol, didodecylphenol, propylene tetramer-substituted phenol, 2,4-dibutylphenol, 2-chlorophenol, dihydroxybiphenyl, catechol, resorcinol, and cresol. Phenol and alkylated phenols having up to 3 alkyl substituents are preferred. Each of the alkyl substituents may contain from 1 to 11, or more, carbon atoms.

The alcohol from which the oxyalkylenated sulfates may be derived is a $C_1$-$C_{40}$ aliphatic alcohol, preferably an alkanol containing about 1–20 carbon atoms and 0–10 nitrogen atoms, e.g., amino-alkanols. They may be monohydric alcohols such as methanol, ethanol, isooctanol, dodecanol, cyclohexanol, cyclopentanol, neopentyl alcohol, isobutyl alcohol, 2-methylcyclohexanol, beta-chloroethanol, monomethyl ether of ethylene glycol, monobutyl ether of ethylene glycol, monopropyl ether of diethylene glycol, monodecyl ether of triethylene glycol, monooleate of ethylene glycol, monostearate of diethylene glycol, sec-pentyl glycol, monostearate of diethylene glycol, sec-pentyl alcohol, tert-butyl alcohol, bromo-decanol, nitro-octadecanol, amino ethanol, and dioleate of glycerol. The polyhydric alcohols contain from 2 to about 10 hydroxy groups and are illustrated by such polyols as ethylene glycol, diethylene glycol, triethylene glycol, tetraethylene glycol, dipropylene glycol, tripropylene glycol, dibutylene glycol, tributylene glycol, and other alkylene glycols in which the alkylene radical contains from 2 to about 8 carbon atoms. Other useful polyhydric alcohols are illustrated by glycerol, mono-oleate of glycerol, monostearate of glycerol, monomethyl ether of glycerol, pentaerythritol, 9,10-dihydroxy stearic acid, methyl ether of 9,10-dihydroxy stearic acid, 1,2-butanediol, 2,3-hexanediol, pinacol, erythritol, arabitol, sorbitol, mannitol, and 1,2-cyclohexanediol.

The amino-alcohols contain about 1–10 nitrogen atoms, including amino-alkylene and amino-arylenesubstituted alcohols. They are exemplified by aminoethanol, 3-aminoethylpentanol, di(hydroxy ethyl) amine, p-aminophenol, tri(hydroxy propyl) amine, N-hydroxyethyl ethylene diamine, N,N,N',N'-tetrahydroxyethyl trimethylene diamine, and N,N,N',N'-tetrahydroxyethyl ethylene diamine. Preferred amino-alcohols are amino-alkanols which contain 1 to 4 hydroxy groups, 1 to 10 nitrogen atoms, and about 1 to 20 carbon atoms.

The corresponding thiols for each of the above alcohols and hydroxy aromatic compounds are equally useful for the preparation of compositions within the scope of this invention.

The preferred sulfates are derived from polyoxyalkylenated alcohols which before oxyalkylenation contain from 1 to about 20 carbon atoms. For the most part, polyoxyalkylene alcohols having up to about 150 oxyalkylene radicals in which the alkylene contains from 2 to about 8 carbon atoms are preferred. The polyoxyalkylene alcohol or phenol may be a polyoxyethylene, polyoxypropylene or polyoxyethylene/polyoxypropylene copolymer, such as the polyoxyethylenepolyoxypropylene block copolymer alcohols, glycols and glycolethers. The number of oxyalkylene units in a given polyoxyalkylene alcohol or phenol varies, but the average total molecular weight of the composition falls in the range of about 500 to about 5000 after sulfation.

The polyoxyethylene/polyoxypropylene block copolymers are particularly preferred. Such copolymers are "amphipathic" in that their structure comprises two dissimilar groups, e.g., water-solubilizing oxyethylene groups and the more hydrophobic oxypropylene groups. In addition, the compositions of this invention include the anionic sulfate group which is also believed to by hydrophilic. The composition, solubility properties, location, relation and relative percentages of these dissimilar moieties in relation to the over-all molecular configuration can serve to determine their relative efficacy as auxiliary inhibitors in rust, corrosion and varnish control, and therefore the preference for a particular sulfate. Although the formation of a haze will, in general, not have a deleterious effect on the lubricating properties of the compounded oil, such haze is considered a source of potential problems such as filter plugging. Consequently, the most preferred sulfates of the present invention are those which at normal concentration levels as auxiliary rust inhibitors do not produce a haze in the fully compounded oil. The most preferred polyoxyalkylene alcohols incorporate about 10–90% weight of oxyethylene units and about 90–10% weight of oxypropylene units.

The alcohols or aromatic hydroxy compounds are oxyalkylenated or polyoxyalkylenated by means which are well known in the art as by reaction with ethylene oxide and/or propylene oxide. The preferred alcohols are selected from $C_1C_{20}$ alcohols such as butanol, octanol, etc., or alternatively the hydroxy derivatives of naturally occurring materials such as lauryl, stearyl and myristyl alcohol, or mixtures of these. The preferred aromatic hydroxy compounds are selected from phenol and $C_1$-$C_{20}$ alkyl-substituted phenols, most preferably $C_1$-$C_{17}$ alkyl-substituted phenols.

The most preferred alcohols are $C_2$-$C_{20}$ polyols having about 2 to 4 hydroxy groups, e.g., diols or glycols, glycerols or triols, and such tetrahydric alcohols as pentaerythritol. The particularly preferred auxiliary rust inhibitors in the practice of this invention are derived from sulfates of polyoxyalkylene polyols containing 2–20 carbon atoms before oxyalkylenation and having from 2 to 4 hydroxyl groups and a total molecular weight after sulfation of about 500 to about 5000. 1,2-gylcols, 1,3-glycols and alpha,omega-glycols are encompassed among the preferred $C_2$-$C_{20}$ polyols. Particularly preferred compositions are selected from the group of polyoxyalkylenated glycol, glycerol, or pentaerythritol having molecular weights from about 500 to about 5000.

The preparation of the polyoxyalkylenated sulfate salts or sulfuric acids for use in this invention is described in U.S. Ser. No. 451,258, filed Mar. 14, 1974 U.S. Pat. No. 3,954,639, the disclosure of which is hereby incorporated by reference.

The salts of this invention are Group II metal salts, preferably calcium, barium or magnesium salts, more preferably calcium or magnesium, and most preferably calcium salts.

While not wishing to be limited by this description, the compositions of this invention probably comprise a complex mixture of at least three components. These components are:

Group II metal salts of an oil-soluble hydrocarbyl sulfonic acid.

Group II metal salts of a polyoxyalkenylated sulfuric acid.

A hybrid salt, possibly having the structural formula hydrocarbyl $SO_3^-(M^{++}—OSO_3\ PAR\ O_3SO—M^{++})_x$ —$O_3S$ hydrocarbyl wherein PAR = polyoxyalkylenated residue In the above formula, the group $M^{++}$ refers to the Group II metal cation. The group hydrocarbyl $SO_3$— refers to the oilsoluble hydrocarbyl sulfonate anion, and the $O_3SO$ polyoxyalkylenated residue refers to the sulfate anion of the polyoxyalkylenated alcohol or aromatic hydroxy compound as described herein, and $x$ is 1 to 10, preferably 1 to 5.

The salts of this invention are prepared by reacting a mixture of a Group I metal, ammonium or other labile such as the triethylammonium salt of the sulfuric acid from the polyoxyalkylenated alcohol or aromatic hydroxy compound described above with an oil-soluble hydrocarbyl sulfonic acid in the presence of an inorganic Group II metal salt. Preferably the metal salt is a halide, e.g., calcium chloride, barium chloride, etc. The molar ratio of the reactants in this process is usually from 1.0–2.0 mols of the hydrocarbyl sulfonic acid to about 1.0–2.5 mols of an inorganic Group II metal salt and from 0.8–1.2 mols of said sulfate. Preferably from 1.0–1.7 mols of the hydrocarbyl sulfonic acid salt is reacted with about 1 mol of said sulfate and 1 mol of said inorganic Group II metal salt.

The reaction may be carried out in the presence of a solvent inert to the reaction such as isobutyl alcohol and other aliphatic alcohols. The sulfonic acid salt ordinarily is added to the reaction mixture as a petroleum oil solution. The reaction is normally carried out at a temperature of 25° to 100° C and at atmospheric pressure; however, higher or lower pressures may be used, as desired. The reaction ordinarily proceeds to completion in about 1 to 10 hours.

In an oil of lubricating viscosity, the compounds of this invention may be used alone as a rust inhibitor or in combinations of 2 or more or in combination with conventional rust inhibitors. The lubricating oil can be any relatively inert and stable fluid of lubricating viscosity. Such lubricating fluids generally have viscosities of 35–50,000 Saybolt Universal Seconds (SUS) at 100° F (38° C). The fluid medium or oil may be derived from either natural or synthetic sources. Included among the natural hydrocarbonaceous oils are paraffin-based, naphthenic-based or mixed-base oils. Synthetic oils include polymers of various olefins, generally of 2 to 6 carbon atoms, alkylated aromatic hydrocarbons, etc. Non-hydrocarbon oils include polyalkylene oxide, carboxylates, phosphates, aromatic ethers, silicones, etc. The preferred media are the hydrocarbonaceous media, both natural and synthetic. Preferred are those hydrocarbonaceous oils having viscosities of about 100–4000 SUS at 100° F. The compatibility of the additives of the present invention within the lubricating medium is evident, among other things, by a lack of haze.

The lubricating oils will be present at 75%, or greater, by weight in the final lubricating composition. In concentrates, however, the oil may be present in from 5 to 75% weight. These concentrates are diluted with additional oil prior to being placed in service to obtain the desired concentration of additives therein.

The Group II metal salts of the present invention are present in the lubricating oil composition in a rust-inhibiting amount. A rust-inhibiting amount will usually run from about 10 ppm to about 10,000 ppm, and preferably from 50–100 ppm to about 5000 ppm.

A preferred lubricating composition will contain sufficient alkaline earth metal carbonate dispersed in a hydrocarbon oil to provide an alkalinity value of 0.5–100 mg of KOH/g. The alkaline earth metal carbonates are magnesium, calcium and barium carbonates, preferably calcium and barium carbonate. Small amounts of the hydroxides of the metals may also be present, usually not contributing more than about 20% of the alkalinity value from the alkaline earth metal composition. These compounds may be dispersed with dispersants that are well known, such as sulfonate, phenate and succinimide dispersants.

Other known additives are desirably included in the composition. Such additives include rust and corrosion inhibitors, antioxidants, oiliness agents, detergents, dispersants, antiwear agents, viscosity index improvers, and pour point depressants. Usually such individual additives will be present in the range of about 0–5% by weight, more generally in the range from about 0–2% by weight, of the total composition. Such typical additional additives found in compositions of the present invention include alkyl succinimide dispersants, phenolic and aryl amine antioxidants, and zinc dihydrocarbyl dithiophosphates.

EXAMPLES

The following examples illustrate the preparation of the salts of this invention and their use in lubricating oils. The examples are provided for the purpose of illustration only, and are not intended to limit the scope of the invention.

EXAMPLE 1

To a 1-liter, 3-neck flask was charged 200 ml of acetone and 97.1 g of sulfamic acid. This mixture was heated to reflux with stirring, and then 475 g of Pluronic L-31 (polyoxyethylene-polyoxypropylene block copolymer diol based on propylene glycol, having a total molecular weight of about 1000 and containing about 10–14% weight oxyethylene and the remainder oxypropylene groups) was added. Acetone was distilled off until the bottoms reached 100° C. Taken overhead was 153 ml of material and 47 ml was left in the pot. The condenser was turned up and continued at 100° C at gentle reflux. As the fluid thickened, the temperature had a tendency to rise, and less solvent refluxed. The reaction mixture was held at 100° C for a total of 4 hours. It was stripped for ¼ hour under vacuum and diluted with a volume of toluene and filtered throught Celite diatomaceous earth. The product was stripped at 100° C at 1 mm Hg.

To a 1-liter, 3-neck flask was added 300 g of the product prepared in the paragraph above. 35 g of sodium hydroxide was added as a 50.8% solution in water. A volume of benzene was added and the mixture was azeotroped until dry. The product was filtered through Celite diatomaceous earth and stripped to 85° C at 1.5 mm Hg. The product is the sodium polyoxyalkylene sulfate.

EXAMPLE 2

To a 1-liter flask under nitrogen was added 475 g of Pluronic L-31. To this was added 100 ml of acetone and 97.1 g of sulfamic acid. The reaction mixture was refluxed for 4¼ hours to maximum temperature of 182° F. A volume of toluene was added and the reaction mixture was filtered and stripped to yield 526 g of product.

To 150 g of the product prepared above in a 3-neck flask was added 50 ml of triethylamine and 200 ml benzene. The mixture was stirred thoroughly and set aside overnight under a slow nitrogen purge. The mixture was then refluxed for 9 hours, stripped to 80° C at 1 mm Hg to yield 162 g of product.

To 111 g of the amine salt of the poly(oxyalkylene) sulfuric acid prepared above was added 96.4 g of sodium SHA 390 sulfonate (a synthetic heavy-alkylated aromatic compound composed primarily of benzene alkylated by one or more alkyl groups, the average number of carbon atoms in the molecule being 21). The mixture was diluted with 1 volume of isobutyl alcohol and 300 ml of 0.5-N sodium hydroxide was added. The mixture was stirred at gentle reflux for 30 minutes; then 100 ml of 1.0 M calcium chloride was added. The mixture was azeotroped until the water coming off was no longer strongly basic. The water phase was separated and discarded. The remaining solution was returned to the flask and 200 ml of 1 molar calcium chloride solution was added. The reaction mixture was stirred at gentle reflux for 1 hour. Water was separated and discarded. The reaction mixture was then again treated with 200 ml of 1 M calcium chloride, stirred at gentle reflux for 1 hour and the water layer separated and discarded. The product was washed 2 times with 400 ml of water, dried over Drierite, filtered and stripped for 30 minutes at 1.5 mm Hg to a bottoms temperature of 90° C.

The product salt is an extremely viscous fluid having a strong IR peak at about 1120 $cm^{-1}$. The salt was placed in Citcon 30 neutral oil at a concentration of 30.1%. This lubricating oil concentrate of the product salt contains 1.68% calcium and 0.012% sodium.

EXAMPLE 3

To 84.2 g of the sodium salt prepared in Example 1 in a 1-liter, 3-neck flask was added 127 g of sodium SHA 390 sulfonate and 1 volume of isobutyl alcohol. The reaction mixture was heated with stirring and 250 ml of 1 M calcium chloride and 100 ml water was added. The reaction mixture was stirred at reflux for 1 hour, decanted into a separatory funnel and the water layer was removed. The addition of calcium chloride and water followed by the removal of water in a separatory funnel was repeated twice. The reaction mixture was then washed 3 times with 200 ml water and stripped under vacuum to yield 132 g of product containing 1.97% Ca and 0.03% Na.

EXAMPLE 4

To a 2-liter, 3-neck flask was added 1200 g Pluronic L-31 and 400 ml acetone. The solution was stripped dry and 210 ml of acetone was added, so that the reflux temperature was 94° C. To this solution was added 246 g of 99% sulfamic acid. The mixture was stirred at gentle reflux overnight and then the acetone was stripped off at half-vacuum to 110° C bottoms. The product was dissolved in toluene, filtered and stripped to yield a bright black product.

191 g of the product prepared above was added to a 2-liter, 3-neck flask and diluted with 1 volume of secondary butanol. To this mixture was added 0.30 mols of NaOH (23.7 g as a 50.8% solution in water) and 318 g of sodium SHA 390 sulfonate. The reaction mixture was stirred thoroughly and heated to reflux. Water was removed during refluxing and then 250 ml of 1.0 M solution of magnesium chloride hexahydrate in water and 100 ml of toluene were added. After refluxing for 2 hours, the reaction mixture was placed in a separatory funnel. The water phase was separated and discarded. To the remaining reaction mixture was added 250 ml of 1.0 M magnesium chloride solution. The mixture was refluxed for 1 hour and the water was again separated and discarded. 250 ml of a 1.0 molar magnesium chloride solution was again added and the mixture refluxed for 1 hour. The water phase was separated and discarded and the product is then washed 3 times with 400 ml of water. The product was stripped under vacuum to yield a very viscous product containing 1.05% Mg and 0.13% Na.

Evaluation

The Neutralization Rate Test (NRT) has been described in U.S. Pat. No. 3,784,474 and Canadian Pat. No. 911,420. The Neutralization Rate Test consists of the neutralization of an acidic aqueous phase with a basic oil phase. The progress of the neutralization is followed with a pH meter by measuring the pH at convenient time intervals. The pH is plotted versus the time. Basic lubricating compositions will neutralize the acid and exhibit a definite point of inflection, usually in the pH range of 3.5 to 6.5, but the time elapsed to the point of inflection (TPI) varies widely depending on the presence or absence of a neutralization promoter of the present invention, all other test factors being kept constant.

The time elapsed from the initial mixing of basic oil and acidic aqueous phases to the point of inflection is the TPI and it forms the basis for comparing various oil compositions. In general, in the comparison of two oil compositions, the one with a low TPI rating (faster acid neutralization) has been found to have greater rust inhibitory capacity than the composition with the higher TPI (slower acid neutralization) all other factors being kept constant. In this test, the rate of stirring and oil viscosity can also affect the rate of neutralization. Typical repeatability is plus or minus 5% of the mean time to point of inflection. The test is regarded as reliable for screening auxiliary rust inhibitors for engine testing, with which it tends to show a partial correlation.

Neutralization Rate Test data is given in Table I. The acidic aqueous phase consisted of 0.004 HCl. The TPI is the minutes to point of inflection in pH versus time curve.

Formulation A being tested is a mixture in Citcon 30 neutral lubricating oil of 6% of a conventional succinimide dispersant, 50 mmols/kg of a calcium phenate and 18 mmols/kg of a zinc dialkyldithiophosphate. Formulated oil B is a mixture in Citcon 30 neutral lubricating oil of 6% of a conventional succinimide dispersant, 25 mmols/kg of a calcium phenate, 25 mmols/kg of an overbased calcium sulfonate and 18 mmols/kg of a zinc dialkyldithiophosphate. The results of this test are reported in Table I below.

TABLE I

Neutralization Rate Test

1. Formulated oil A with no rust inhibitor — TPI, 116 min.
2. Formulated oil A with 0.1% wt of the composition of Example 3 — TPI, 56 min.
3. Formulated oil A with 0.1% wt of the composition of Example 4 — TPI, 30 min.
4. Formulated oil B with 0.1% wt of the composition of Example 3 — TPI, 34 min.

The salts of Examples 3 and 4 were further evaluated, in comparison to known rust inhibitors, in the General Motors Sequence IIC rust test. The test oil is a R.I. Sun Puerto Rico SAE 30 lubricating oil containing 6% of a conventional succinimide dispersant, 25 mmols/kg of an overbased calcium sulfonate, 25 mmols/kg of a calcium phenate, and 18 mmols/kg of a zinc dialkyldithiophosphate. The test oil is blended with the anti-rust compound as noted in Table II. The average engine rust (AER) is measured after 32 hours and the number of stuck rings is noted. GM specifications require at least an AER rating of 8.4 to pass the test.

TABLE II

| | Rust-inhibiting Component | Sequence IIC AER rating | Stuck Rings |
|---|---|---|---|
| 500 ppm | Pluronic L-31 sulfate | 6.4 | 16 |
| 1000 ppm | " | 7.4 | 13 |
| 0.25% | NI-W sulfate (monoalkylphenylpolyoxyethylene ether sulfate) | 7.3 | 11 |
| 1000 ppm | Carbowax E750 sulfate | 7.6 | 0 |
| 600 ppm | Product of Example 3 | 7.9 | 0 |
| 600 ppm | Product of Example 4 | 7.9 | 0 |

What is claimed is:

1. A Group II metal salt of:
   A. an oil-soluble hydrocarbyl sulfonic acid; and
   B. a polyoxyalkylenated sulfuric acid having a molecular weight in the range of about 500 to about 5000.

2. A compound according to claim 1 wherein said oil-soluble hydrocarbyl sulfonic acid is a petroleum sulfonic acid, a polyalkyl benzene sulfonic acid or a polyalkylene sulfonic acid and said Group II metal is calcium, barium or magnesium.

3. A compound according to claim 2 wherein said polyoxyalkylenated sulfuric acid is a polyoxyalkylenated sulfuric acid from a polyoxyalkylenated alcohol or amino-alkanol of 1 to 20 carbon atoms and 0 to 10 nitrogen atoms and said hydrocarbyl sulfonic acid is a polyalkylbenzene sulfonic acid or a polyisobutenyl sulfonic acid.

4. A compound according to claim 3 wherein said alcohol is a polyhydric alcohol containing from 2 to about 10 hyroxy groups and said Group II metal is calcium or magnesium.

5. A compound according to claim 4 wherein said polyoxyalkylenated sulfuric acid is a polyoxyalkylenated sulfuric acid from a polyoxyethylene polyol, a polyoxypropylene polyol, or a polyoxyethylene/polyoxypropylene block copolymer polyol.

6. A compound according to claim 5 wherein said polyol is a $C_2$–$C_{20}$ polyol containing from 2 to 4 hydroxyl groups, said sulfonic acid is a polyalkylbenzene sulfonic acid, and said Group II metal is calcium.

7. A compound according to claim 4 wherein said polyoxyalkylenated alcohol is polyoxyalkylene glycol, polyoxyalkylene glycerol or polyoxyalkylene pentaerythritol.

8. A lubricating composition comprising an oil of lubricating viscosity and an effective amount of a compound of claim 1 or mixtures thereof.

9. A lubricating composition according to claim 8 wherein said oil-soluble hydrocarbyl sulfonic acid is a petroleum sulfonic acid, a polyalkylbenzene sulfonic acid or a polyalkylene sulfonic acid and said Group II metal is calcium, barium or magnesium.

10. A lubricating composition according to claim 9 wherein said polyoxyalkylenated sulfuric acid is a polyoxyalkylenated sulfuric acid from a polyoxyalkylenated alcohol or amino-alkanol of 1 to 20 carbon atoms and 0 to 10 nitrogen atoms and said hydrocarbyl sulfonic acid is a polyalkylbenzene sulfonic acid or a polyisobutenyl sulfonic acid.

11. A lubricating composition according to claim 10 wherein said alcohol is a polyhydric alcohol containing from 2 to about 10 hydroxy groups and said Group II metal is calcium or magnesium.

12. A lubricating composition according to claim 11 wherein said polyoxyalkylenated sulfuric acid is the polyoxyalkylenated sulfuric acid from a polyoxyethylene polyol, a polyoxypropylene polyol, or a polyoxyethylene/polyoxypropylene block copolymer polyol.

13. A lubricating composition according to claim 12 wherein said polyol is a $C_2$–$C_{20}$ polyol containing from 2 to 4 hydroxyl groups, said sulfonic acid is a polyalkylbenzene sulfonic acid and said Group II metal is calcium.

14. A lubricating composition according to claim 11 wherein said polyoxyalkylenated alcohol is polyoxyalkylene glycol, polyoxyalkylene glycerol, or polyoxyalkylene pentaerythritol.

15. A method for the preparation of salts which comprises treating from 1.0 to 2.0 mols of a salt of an oil-soluble hydrocarbyl sulfonic acid with 0.8 to 1.2 mols of a Group I metal salt of a polyoxyalkylenated sulfuric acid having a molecular weight in the range of about 500 to about 5000, and from 1.0 to 2.5 mols of an inorganic Group II metal salt.

16. A method for the preparation of lubricating oil compositions which comprises blending a compound according to claim 1 with a lubricating oil.

17. The product prepared by the process of claim 15.

* * * * *